United States Patent
Suzuki et al.

(10) Patent No.: US 10,602,997 B2
(45) Date of Patent: Mar. 31, 2020

(54) RADIOGRAPHING APPARATUS AND RADIOGRAPHING SYSTEM

(71) Applicant: CANON KABUSHIKI KAISHA, Tokyo (JP)

(72) Inventors: Masataka Suzuki, Kawasaki (JP); Takaaki Gonda, Yokohama (JP); Masaaki Kobayashi, Shimotsuke (JP); Shichihei Sakuragi, Tokyo (JP); Hiroto Kondo, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 342 days.

(21) Appl. No.: 15/494,295

(22) Filed: Apr. 21, 2017

(65) Prior Publication Data

US 2017/0311913 A1 Nov. 2, 2017

(30) Foreign Application Priority Data

Apr. 28, 2016 (JP) .................. 2016-091606

(51) Int. Cl.
*A61B 6/10* (2006.01)
*A61B 6/00* (2006.01)
*G03B 42/04* (2006.01)
*G01T 7/00* (2006.01)
*H02J 7/00* (2006.01)

(52) U.S. Cl.
CPC ............ *A61B 6/4283* (2013.01); *A61B 6/102* (2013.01); *A61B 6/4216* (2013.01); *G01T 7/00* (2013.01); *G03B 42/04* (2013.01); *H02J 7/0044* (2013.01); *H02J 7/0052* (2013.01)

(58) Field of Classification Search
CPC ..... A61B 6/102; A61B 6/4216; A61B 6/4283; G01T 7/00; G03B 42/04; H02J 7/0044; H02J 7/0052
See application file for complete search history.

(56) References Cited

U.S. PATENT DOCUMENTS

2013/0083898 A1* 4/2013 Tajima ................. A61B 6/4283
378/97
2015/0293239 A1* 10/2015 Miyoshi .................... G01T 7/00
250/394

FOREIGN PATENT DOCUMENTS

JP 4617017 B2 1/2011

* cited by examiner

*Primary Examiner* — Mark R Gaworecki
(74) *Attorney, Agent, or Firm* — Canon USA, Inc., IP Division

(57) ABSTRACT

A radiographing apparatus includes a radiation detection panel including an effective image-acquisition area configured to detect radiation and a casing configured to house the radiation detection panel. The casing includes an incidence surface on which the radiation is incident, a back surface opposite the incidence surface, and a side surface between the incidence surface and the back surface. On the side surface of the casing, a level-difference portion indicating a position based on the effective image-acquisition area and a protrusion protruding more outward than the level-difference portion are provided.

20 Claims, 8 Drawing Sheets

RADIOGRAPHING APPARATUS AND RADIOGRAPHING SYSTEM

BACKGROUND OF THE INVENTION

Field of the Invention

The present disclosure relates to a radiographing apparatus including a radiation detection panel and a radiographing system including the radiographing apparatus.

Description of the Related Art

Radiographing apparatuses that detect intensity distribution of radiation that has passed through an object to acquire a radiographic image are generally widely used in non-destructive inspection for industrial use and medical diagnostics.

Radiographing apparatuses take radiographs in a state in which the irradiation area of radiation emitted from a radiation source, the effective image-acquisition area of the radiographing apparatus, and the position of the object to be radiographed are aligned. For the purpose of alignment, an operator needs to easily recognize the effective image-acquisition area of the radiographing apparatus.

Japanese Patent No. 4617017 discloses a radiographing apparatus in which indicators with different level-difference or different frictional resistances are provided on the side surface of the casing to allow tactile recognition of the effective image-acquisition area of the radiographing apparatus.

However, the radiographing apparatus disclosed in Japanese Patent No. 4617017 may not take sufficient measures for protecting the casing during handling. For example, while aligning the radiographing apparatus, a level-difference portion formed as an indicator could be caught on a bed or table for radiographing and damage the casing.

SUMMARY OF THE INVENTION

The present disclosure provides a radiographing apparatus with a level-difference portion indicating an effective image-acquisition area, in which an external impact to the level-difference portion is reduced or eliminated.

According to an aspect of the present disclosure, a radiographing apparatus includes a radiation detection panel including an effective image-acquisition area configured to detect radiation and a casing configured to house the radiation detection panel. The casing includes an incidence surface on which the radiation is incident, a back surface opposite the incidence surface, and a side surface between the incidence surface and the back surface. On the side surface of the casing, a level-difference portion indicating a position based on the effective image-acquisition area and a protrusion protruding more outward than the level-difference portion are provided.

Further features of the present disclosure will become apparent from the following description of exemplary embodiments with reference to the attached drawings.

DESCRIPTION OF THE EMBODIMENTS

Embodiments of the present disclosure will be specifically described with reference to the accompanying drawings. However, the dimensions and the details of the structures shown in the embodiments are not limited to those illustrated in the specification and the drawings. In this specification, radiation includes not only X-rays but also β-rays, α-rays, γ-rays, corpuscular rays, and cosmic rays.

First Embodiment

A radiographing apparatus according to a first embodiment will be described with reference to FIGS. 1A and 1B to FIGS. 5A and 5B.

Figure 1A:
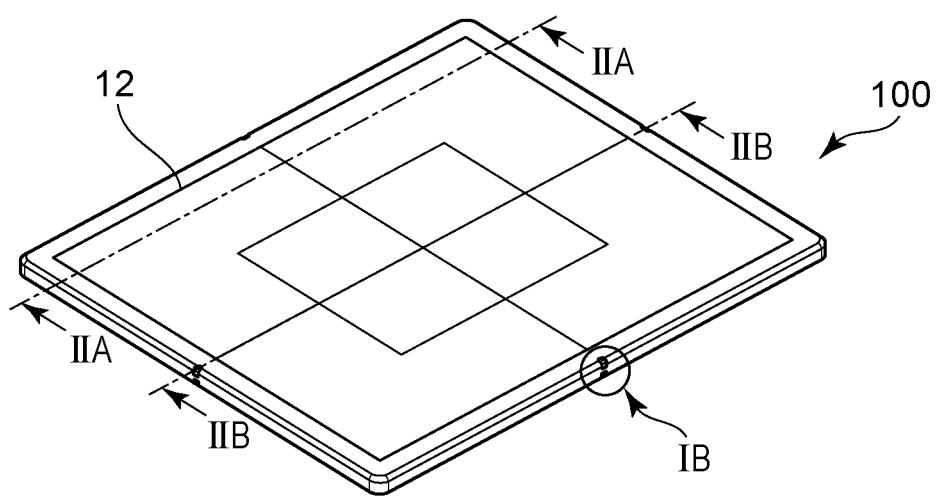
FIG. 1A is an external view of a radiographing apparatus of a first embodiment.
Figure 1B:
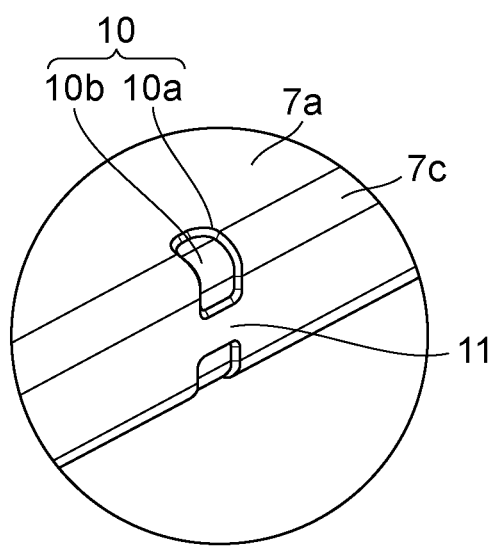
FIG. 1B is a partial enlarged view of the radiographing apparatus in FIG. 1A.
Figure 2A:
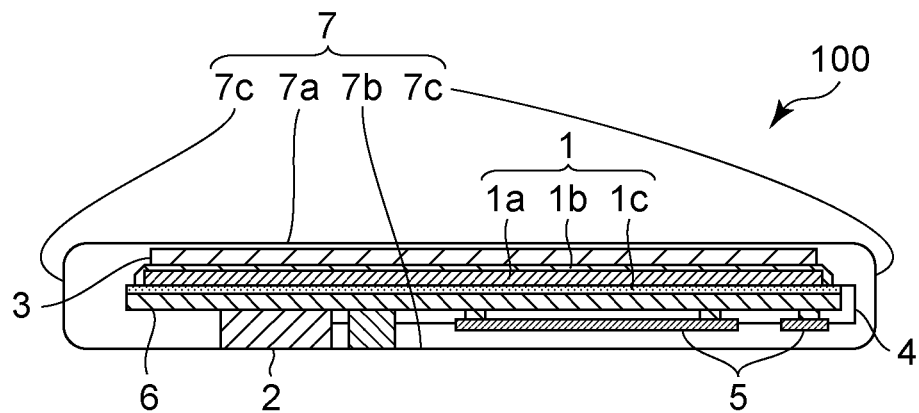
FIG. 2A is a cross-sectional view taken along line IIA-IIA in FIG. 1A.
Figure 2B:
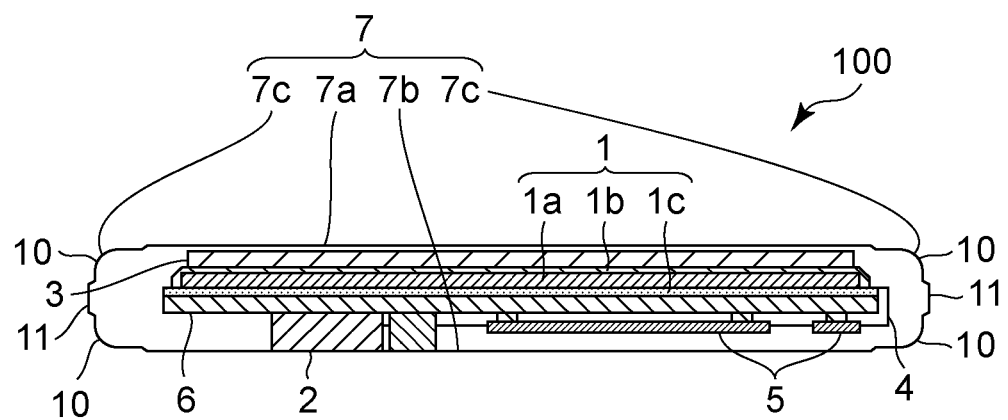
FIG. 2B is a cross-sectional view taken along line IIB-IIB in FIG. 1A.

FIG. 1A is an external view of the radiographing apparatus of the first embodiment. FIG. 1B is an enlarged view of the periphery of part a of the radiographing apparatus in FIG. 1A. FIGS. 2A and 2B are cross-sectional views of the radiographing apparatus of the first embodiment. FIG. 2A is a cross-sectional view taken along line IIA-IIA in FIG. 1A. FIG. 2B is a cross-sectional view taken along line IIB-IIB in FIG. 1A.

A radiographing apparatus 100 acquires a radiographic image according to radiation radiated by a radiation generating apparatus (not shown) and transmitted through an object. The radiographing apparatus 100 transfers the acquired radiographic image to an external unit (a console). The transferred radiographic image is displayed on a display unit or the like, and the quality is checked by the user.

The radiographing apparatus 100 includes a radiation detection panel 1 for converting radiation to an electrical signal. The radiation detection panel 1 has the function of converting the incident radiation to an electrical signal. The radiation detection panel 1 includes a sensor substrate 1c in which a plurality of photoelectric conversion elements are disposed in two dimensions on a glass substrate, a phosphor layer 1a disposed on the sensor substrate 1c, and a phosphor protection film 1b disposed on the phosphor layer 1a. The plurality of photoelectric conversion elements disposed on the sensor substrate 1c are PIN-type or MIS-type conversion elements capable of detecting visible light. The phosphor protection film 1b is made of a material with relatively high moisture resistance and is used to protect the phosphor layer 1a. The radiation detection panel 1 has an effective image-acquisition area in which incident radiation can be imaged as a radiographic image. In the radiation detection panel 1, the whole or part of an area on a surface on which the plurality of photoelectric conversion elements are disposed is defined as the effective image-acquisition area.

With the above configuration, in the radiation detection panel 1, the phosphor layer 1a emits light by the incident radiation, and the photoelectric conversion elements disposed on the sensor substrate 1c convert the emitted light to an electrical signal. The radiation detection panel 1 may include direct conversion type conversion elements that directly convert radiation to an electrical signal instead of the phosphor layer 1a and the photoelectric conversion elements.

The radiation detection panel 1 is electrically connected to a control substrate 5 via a flexible circuit board 4. The control substrate 5 reads the resultant electrical signal from the radiation detection panel 1 and processes the read electrical signal. The control substrate 5 converts the electrical signal to a digital signal to acquire radiographic image data. The radiographing apparatus 100 further includes a secondary battery 2 for supplying electric power for use in operating the radiation detection panel 1 and the control substrate 5. The secondary battery 2 has a function as a battery. Possible examples of the secondary battery 2 include a lithium-ion battery and an electric double layer capacitor.

The above-described components are supported by a support base 6. The support base 6 supports the radiation detection panel 1 on the radiation incidence surface side. The support base 6 supports the control substrate 5, the secondary battery 2 and the like on a surface opposite the surface that supports the radiation detection panel 1. The radiographing apparatus 100 may further include a cushioning material 3 that protects the radiation detection panel 1 from an external force between a casing 7 and the radiation detection panel 1.

The casing 7 houses the above-described components. The casing 7 includes an incidence surface 7a on which radiation is incident, a back surface 7b disposed at a position opposite the incidence surface 7a, with the radiation detection panel 1 therebetween, and a side surface 7c connecting the incidence surface 7a and the back surface 7b together.

The incidence surface 7a may have relatively high radiation transmittance to make radiation incident. Furthermore, the incidence surface 7a may be light in weight and can maintain a certain strength against impact. For that purpose, the incidence surface 7a is made of, for example, a resin material or carbon fiber reinforced plastic (CFRP).

The back surface 7b and the side surface 7c may have sufficient strength against falling and impact, lightweight for reducing burden during transport, and sufficient operability. For example, the back surface 7b and the side surface 7c may be made of metal alloy of magnesium or aluminum, CFRP, or fiber-reinforced resin. Alternatively, the back surface 7b and the side surface 7c may be made of a material with relatively high magnetic permeability, such as SUS430, to effectively reduce noise received from the outside of the casing 7.

On the surface of the incidence surface 7a, an indicator 12 for indicating a central portion and the range of the effective image-acquisition area is formed. The indicator 12 is formed on the surface of the incidence surface 7a by painting or printing process. The user can visually recognize the effective image-acquisition area using the indicator 12. The indicator 12 is not limited to the above and may be a level-difference recessed toward the radiation detection panel 1. Furthermore, on the side surface 7c of the casing 7, level-difference (or cutout) portions 10 are provided corresponding to the effective image-acquisition area. This allows the user to tactually recognize the effective image-acquisition area by touching the level-difference portions 10. For that reason, for example, even if the radiographing apparatus 100 is disposed on the back of the subject by alignment at radiography, so that the indicator 12 cannot be visually recognized, the user can recognize the effective image-acquisition area by touching the level-difference portions 10 from the side surface 7c.

Next, the shape of the level-difference portions 10 will be described. Part of each level-difference portion 10 is formed on the side surface 7c, and the other part is formed across the incidence surface 7a and the back surface 7b. The level-difference portions 10 are preferably 0.5 mm or more in depth and 5 mm or more in width to allow the user to easily tactually recognize them. However, the depth of the level-difference portions 10 is given for mere illustration and may be any other depth that can be given in the side surface 7c and can be tactually recognized by the user when touched.

Each level-difference portion 10 has a recessed shape and includes side walls 10a of the level-difference portion and a bottom surface 10b connecting the side walls 10a together. The bottom surface 10b is disposed at a position intersecting a center line passing through the central coordinates of the effective image-acquisition area. In other words, each level-difference portion 10 and the central coordinates of each of the sides that form the rectangular effective image-acquisition area are disposed so as to be aligned. This allows the user to tactually recognize the central coordinates of the effective image-acquisition area, facilitating alignment at radiography. The level-difference portions 10 are not necessarily disposed at the positions indicating the central coordinates of the effective image-acquisition area but may be disposed so as to indicate any positions in the effective image-acquisition area. In one example, the level-difference portions 10 may be disposed on the extended lines of the ends of the effective image-acquisition area indicated by the indicator 12.

Next, the relationship among the plurality of level-difference portions 10 will be described. The level-difference portions 10 are disposed on the individual four sides of the casing 7 and disposed at symmetrical positions about the central coordinates (central axis) of the effective image-acquisition area. Since the plurality of level-difference portions 10 are disposed at symmetrical positions in this manner, the user can easily adjust the orientation of the radiographing apparatus 100 viewed from the direction of incidence of radiation. Although the plurality of level-difference portions 10 disposed on the individual sides have the same shape, the shape is not limited to that. For example, the width of the bottom surface 10b or the inclination of the side walls 10a may be changed for each side. To facilitate tactile recognition, the bottom surface 10b of each level-difference portion 10 may have different frictional resistance from that of the side surface 7c of the casing 7.

Problems when the level-difference portions 10 are provided on the side surface 7c will be described. When the radiographing apparatus 100 is positioned upright, with the side surface 7c in contact with the ground, and installed while the side surface 7c is slid on a bed, a table, or a charging cradle in alignment at radiography, the level-difference portion 10 can be caught on the contact surface to damage the casing 7. To prevent it, a sliding portion 11 is disposed on each side of the side surface 7c having a level-difference portion 10.

The sliding portion 11 is a protrusion disposed so as to protrude outward from the level-difference portion 10 viewed from the direction of incidence of radiation. The presence of the sliding portion 11 allows the level-difference portion 10 to be disposed on the side surface 7c of the casing 7 so as not to include a central position on the side surface 7c in the thickness direction. Furthermore, the sliding portion 11 forms part of the casing 7 and defines the outermost shape of the side surface 7c of the radiographing apparatus 100. The sliding portion 11 has a structure that is flat with respect to a direction in which the side surface 7c extends. This prevents, even when the radiographing apparatus 100 is positioned upright, with the side surface 7c in contact with a flat surface, and the side surface 7c is slid, the level-difference portion 10 from coming into direct-contact with the ground, thus preventing the level-difference portion 10 from being caught on the ground.

Figure 3A:
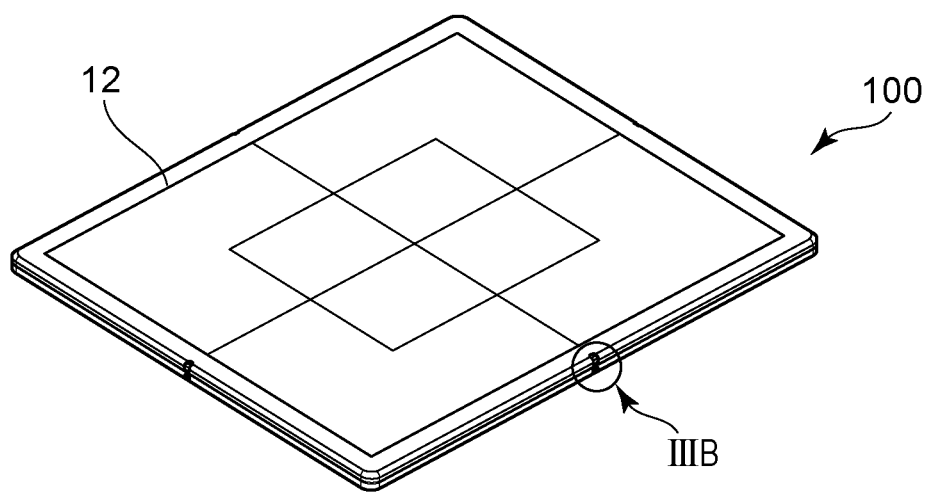
FIG. 3A is an external view of the radiographing apparatus of the first embodiment.
Figure 3B:
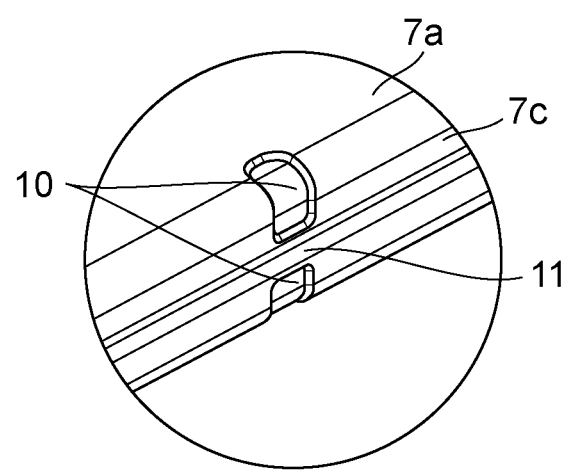
FIG. 3B is a partial enlarged view of the radiographing apparatus in FIG. 3A.

Next, another form of the sliding portion 11 of the first embodiment will be described with reference to FIGS. 3A and 3B. FIG. 3A is an external view of the radiographing apparatus 100 in the first embodiment. FIG. 3B is an enlarged view of part b in the external view of the radiographing apparatus in FIG. 3A.

In FIG. 3B, the sliding portion 11 is disposed so as to protrude outward from the flat portion of the side surface 7c viewed from the direction of incidence of radiation. Therefore, the casing 7 is disposed such that the sliding portion 11, a portion of the side surface 7c that does not function as the sliding portion 11, and the bottom surface 10b of the level-difference portions 10 are disposed in that order viewed from a direction perpendicular to the direction of incidence of radiation (a direction substantially perpendicular to the side surface 7c of the casing 7). The sliding portion 11 is disposed so as to align with the center of gravity of the radiographing apparatus 100 or the center of the radiographing apparatus 100 as viewed from the direction perpendicular to the direction of incidence of radiation. Therefore, the level-difference portion 10 is formed so as to substantially extend from the incidence surface 7a to the back surface 7b, whereas the sliding portion 11 is disposed so as to intersect the level-difference portion 10. This configuration allows the posture of the radiographing apparatus 100 to be stabilized when the radiographing apparatus 100 is slid in a standing condition in contact with a flat surface. Furthermore, the distance from the contact surface to the level-difference portion 10 is larger than that of the structure in FIG. 1. This makes the level-difference portion 10 less likely to be caught on a structure on the contact surface. Furthermore, the level-difference portion 10 may be changed in shape between the incidence surface 7a and the back surface 7b. This allows the user to discriminate between the incidence surface 7a and the back surface 7b by touching the level-difference portion 10. The sliding portion 11 may be disposed at the same position as that of the radiation detection surface of the radiation detection panel 1 viewed from the direction perpendicular to the direction of incidence of radiation. This allows the user to easily estimate the projection state of radiation on the radiation detection panel 1, allowing accurate alignment with the radiation generating apparatus. The casing 7 and the sliding portion 11 may be configured as separate components or the same component. The sliding portion 11 may be configured so that the frictional resistance is lower than the other part of the side surface 7c to make the friction at installation low to allow the radiographing apparatus 100 to be installed with a small external force.

Figure 4A:
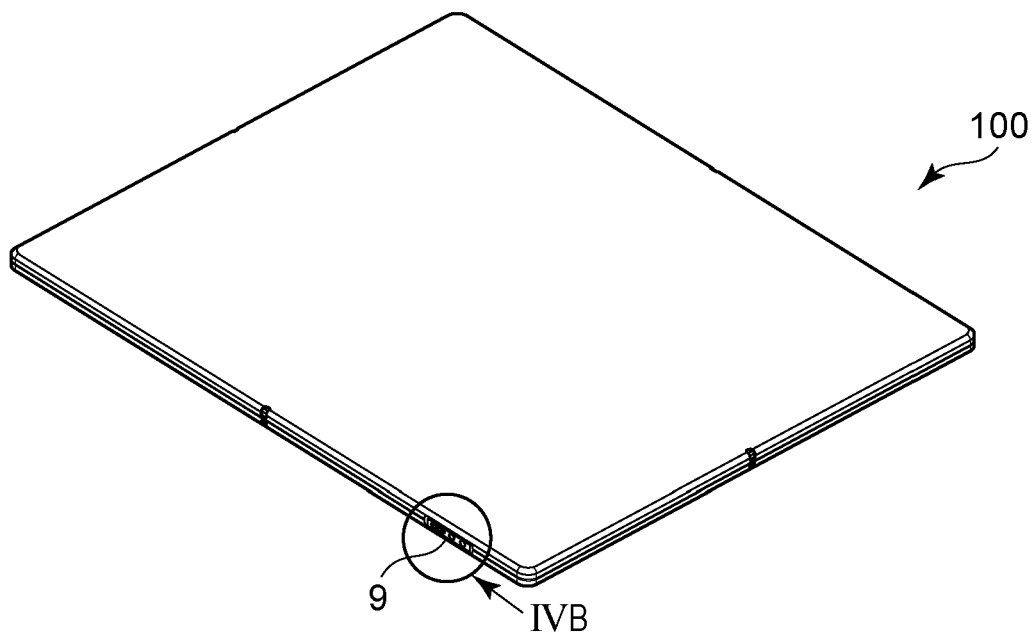
FIG. 4A is an external view of the radiographing apparatus of the first embodiment.
Figure 4B:
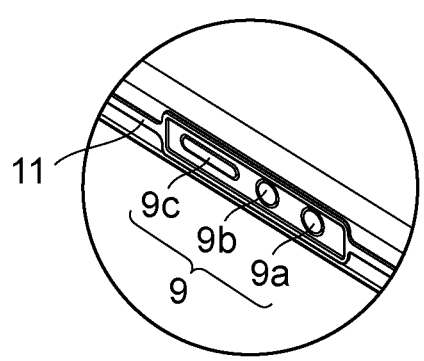
FIG. 4B is a partial enlarged view of the radiographing apparatus in FIG. 4A.

Next, the relationship between an operating unit or a connection (external interface) disposed on the side surface 7c of the casing 7 and the sliding portion 11 will be described with reference to FIGS. 4A and 4B and FIGS. 5A and 5B. FIGS. 4A and 4B are diagrams illustrating the relationship between the operating unit and the sliding portion 11 of the radiographing apparatus 100 of the first embodiment. FIG. 4A is an external view of the radiographing apparatus 100, and FIG. 4B is an enlarged view of part c in the external view of the radiographing apparatus in FIG. 4A. In FIGS. 4A and 4B, the other components on the outer wall of the casing 7 are omitted.

The radiographing apparatus 100 includes an operating unit 9 for operating the radiographing apparatus 100 on the side surface 7c of the casing 7. The operating unit 9 includes a power switch 9a, a state control switch 9b, and a radio communication unit 9c. The power switch 9a receives an input for switching the on-off state of the power supply of the radiographing apparatus 100. The state control switch 9b is used to change the operation mode of the radiographing apparatus 100 and to switch the on/off state of communication with an external unit. The radio communication unit 9c is capable of transmitting and receiving various information to and from the console and communication for coordination with the console. As illustrated in FIGS. 4A and 4B, the outermost periphery of the operating unit 9 is disposed inside the side surface 7c of the casing 7 (the outermost periphery of the casing 7) as viewed from the direction of incidence of radiation.

Figure 5A:
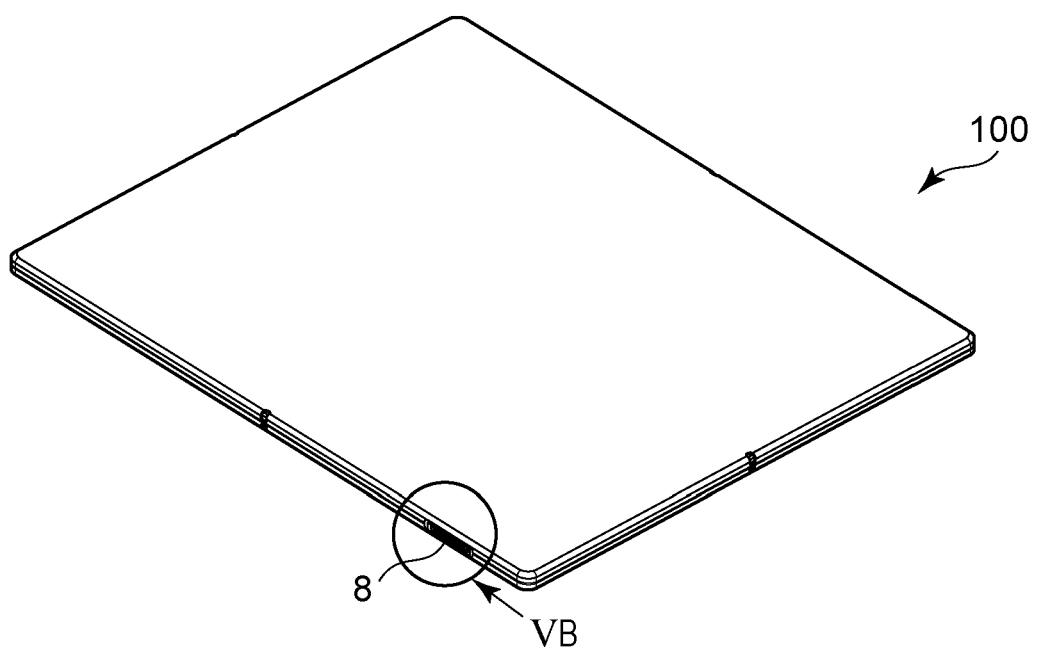
FIG. 5A is an external view of the radiographing apparatus of the first embodiment.
Figure 5B:
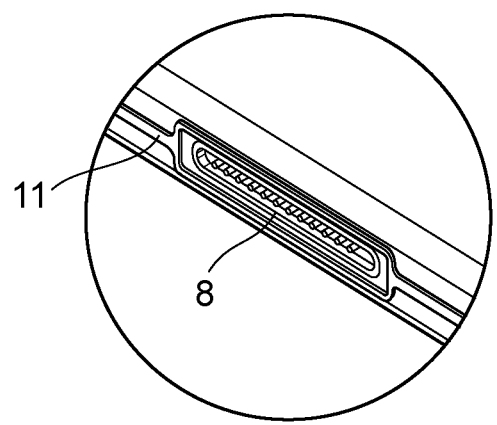
FIG. 5B is a partial enlarged view of the radiographing apparatus in FIG. 5A.

FIGS. 5A and 5B are diagrams illustrating the relationship between the radiographing apparatus 100 and the connection in the first embodiment. FIG. 5A is an external view of the radiographing apparatus 100, and FIG. 5B is an enlarged view of the vicinity of part d in the external view of the radiographing apparatus 100 in FIG. 5A. In FIGS. 5A and 5B, the other components on the outer wall of the casing 7 are omitted.

The radiographing apparatus 100 includes a connection 8 for connecting the radiographing apparatus 100 and an external unit (not shown) to each other on the side surface 7c of the casing 7. The connection 8 functions as an interface during wired communication, for which, for example, a connector is used. The radiographing apparatus 100 is capable of receiving electric power from an external power supply by wired connection via the connection 8. Furthermore, the radiographing apparatus 100 is capable of transmitting and receiving a control signal to and from the console and transferring a radiographic image to the console by wired connection via the connection 8. As illustrated in FIGS. 5A and 5B, the outermost surface of the connection 8 is disposed inside the side surface 7c of the casing 7 (the outermost periphery of the casing 7) as viewed from the direction of incidence of radiation.

Therefore, the sliding portion 11 is disposed outside the operating unit 9 and the connection 8 as viewed from the direction of incidence of radiation. This prevents the operating unit 9 and the connection 8 from being damaged during handling. This prevents the connection 8 and the operating unit 9 from being caught even when the sliding portion 11 is slid on the ground, with the radiographing apparatus 100 in a standing condition.

In this embodiment, the radiographing apparatus has level-difference portions serving as indicators that can be tactually recognized for alignment with the effective image-acquisition area. The outer wall (the sliding portion) of the casing is disposed outside the level-difference portions. This prevents damage to the casing during, for example, handling of the radiographing apparatus 100. This also prevents damage to the connection, the operating unit, and so on during handling of the radiographing apparatus, for example.

Second Embodiment

Figure 6A:
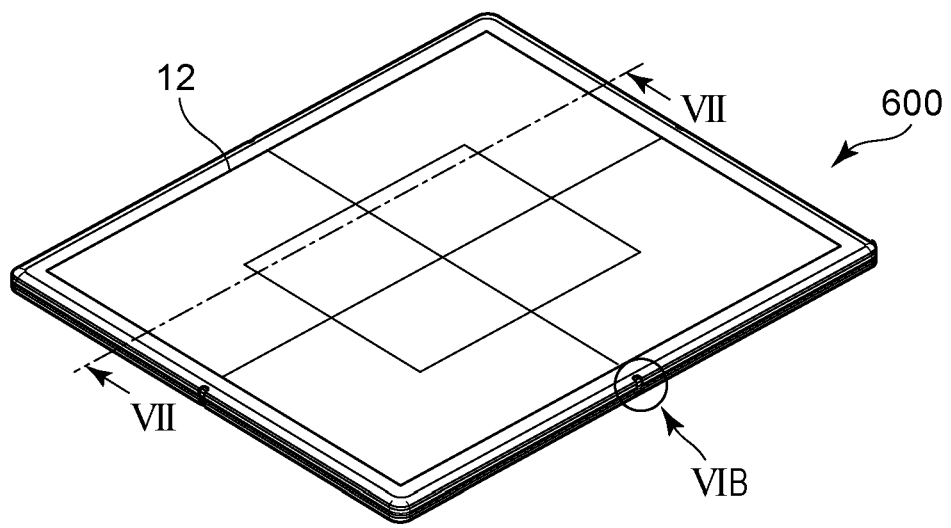
FIG. 6A is an external view of a radiographing apparatus of a second embodiment.
Figure 6B:
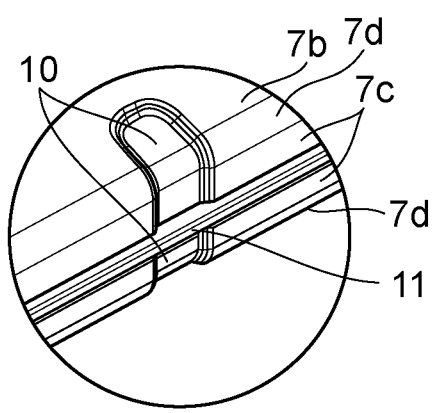
FIG. 6B is a partial enlarge view of the radiographing apparatus in FIG. 6A.
Figure 7:
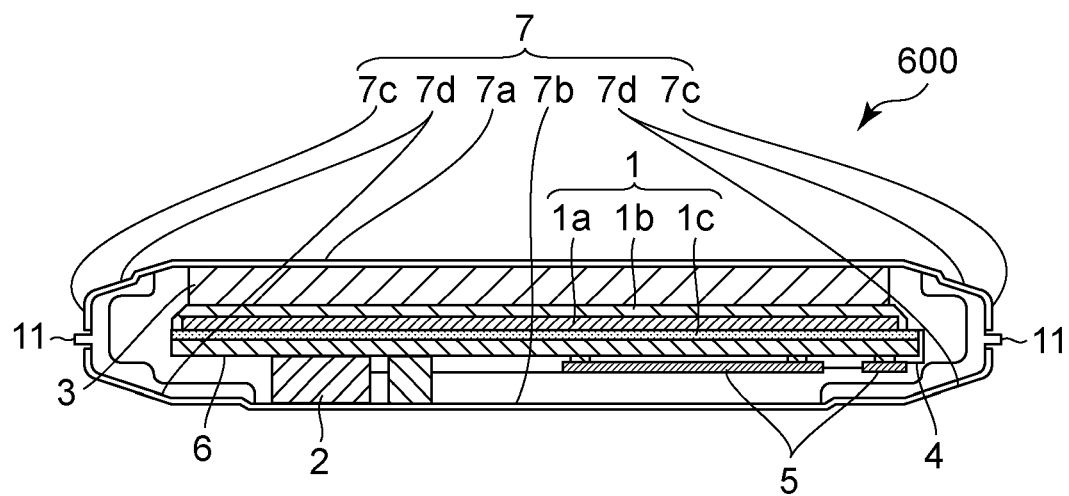
FIG. 7 is a cross-sectional view taken along line VII-VII in FIG. 6A.

A radiographing apparatus 600 according to a second embodiment will be described with reference to FIGS. 6A and 6B and FIG. 7. FIG. 6A is an external view of the radiographing apparatus 600 in the second embodiment, and FIG. 6B is an enlarge view of part e in FIG. 6A. FIG. 7 is a cross-sectional view taken along line VII-VII in FIG. 6A.

The radiographing apparatus 600 in the second embodiment differs from the first embodiment in that the level-difference portions 10 are not disposed on a flat portion of the incidence surface 7a. In the radiographing apparatus 600 of the second embodiment, the level-difference portions 10 are disposed on two inclined surfaces 7d, the side surface 7c, and the back surface 7b of the casing 7 and are not disposed on the incidence surface 7a. Therefore, even when a subject is placed on the incidence surface 7a of the radiographing apparatus 600 (for example, when the subject is radiographed at a posture such as a recumbent position), the subject is difficult to contact the level-difference portions 10. This gives little uncomfortable feeling to the subject during radiography.

Furthermore, even when the radiographing apparatus 600 is positioned upright, with the incidence surface 7a or the side surface 7c in contact with the contact surface as a lower surface, it is easy to insert user's fingers or the like into the level-difference portions 10 disposed on the inclined surfaces 7d, improving convenience.

The sliding portion 11 is made of a different member and is disposed so as to be fixed and supported by the inner wall of the casing 7 such that part thereof protrudes to the outside of the casing 7 as viewed from the direction of incidence of radiation. The configuration of the sliding portion 11 and the casing 7 improves the rigidity of the side surface 7c of the casing 7. This improves resistance to an impact from the outside of the casing 7. Furthermore, since part of the sliding portion 11 is disposed so as to protrude from the casing 7, it is possible to prevent an external force from a direction perpendicular to the side surface 7c from being directly exerted to the casing 7.

Thus, this embodiment is configured such that no level-difference is provided on the incidence surface of the casing as compared with the first embodiment. Therefore, the radiographing apparatus of this embodiment gives little uncomfortable feeling to the subject during radiography. Furthermore, the sliding portion is fixed to the inner wall of the casing, and part of the sliding portion protrudes from the casing. This improves resistance to an impact from the outside of the casing, as compared with the first embodiment.

Application

Figure 8A:
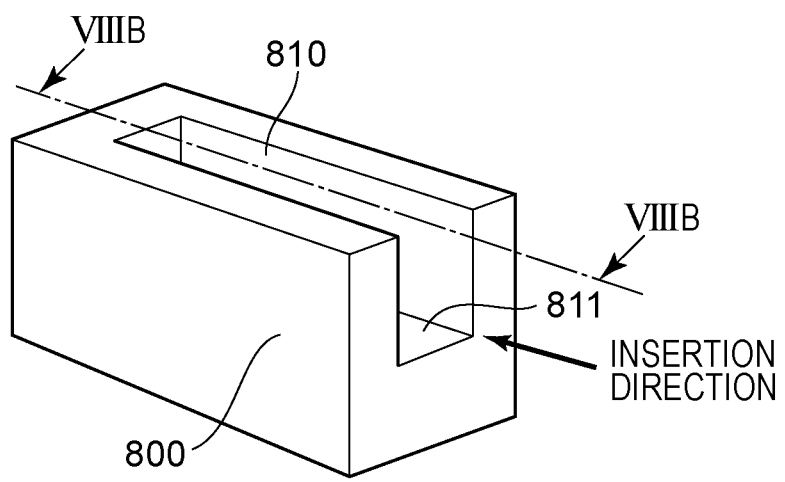
FIG. 8A is an external view of an application of a radiographing apparatus of an embodiment.
Figure 8B:
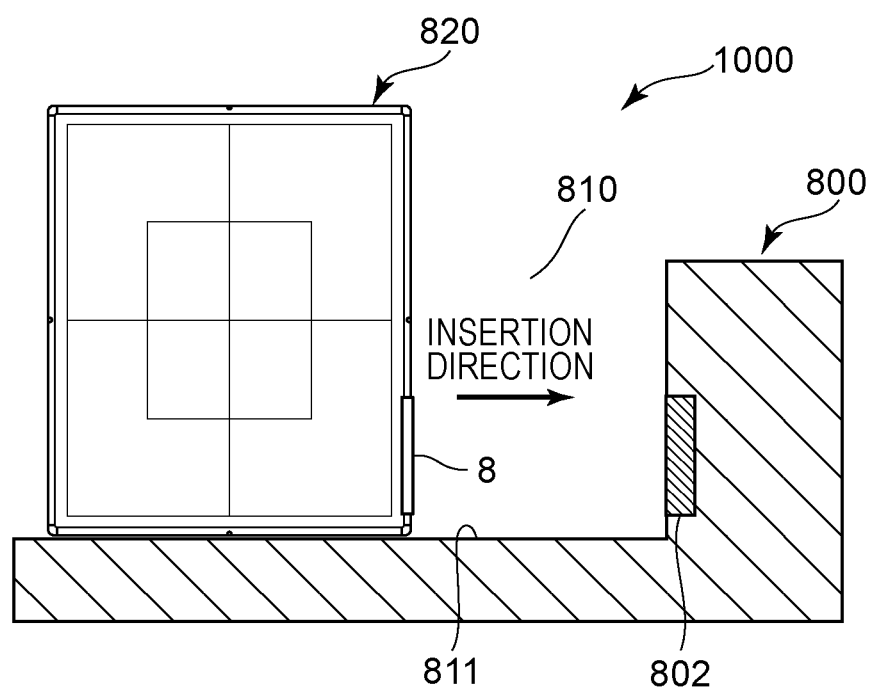
FIG. 8B is a diagram illustrating a state in which the radiographing apparatus is housed in a battery charger.

Referring to FIGS. 8A and 8B, a case in which the radiographing apparatuses in the above embodiment are charged using a battery charger will be described. FIGS. 8A and 8B are diagrams illustrating a radiographing system 1000 which is an application of the radiographing apparatuses. FIG. 8A is an external view of a battery charger 800. FIG. 8B is a diagram illustrating a state in which the radiographing apparatus is housed in the battery charger 800. The battery charger 800 in FIG. 8B is a cross-sectional view of the battery charger 800 in FIG. 8A taken along line VIIIB-VIIIB.

The radiographing system 1000 includes a radiographing apparatus 820 and the battery charger 800. The battery charger 800 includes a housing unit 810 for housing the radiographing apparatus 820 and a connection 802 for connecting with the radiographing apparatus 820. The battery charger 800 electrically connects the connection 802 with the connection 8 of the radiographing apparatus 820 in a state in which the radiographing apparatus 820 is housed in the housing unit 810 to charge the secondary battery 2 built in the radiographing apparatus 820.

Next, a case in which the radiographing apparatus 820 is housed in the battery charger 800 will be described. The radiographing apparatus 820 is housed after one side of the casing 7 is brought into contact with a bottom surface 811 of the housing unit 810 and moved so as to be slid in an insertion direction. This can cause the level-difference portion 10 of the radiographing apparatus 820 to be caught on the bottom surface 811 to damage the casing 7. For that reason, as described in the first and second embodiments, the radiographing apparatus 820 is housed such that the sliding portion 11 is slid in contact with the bottom surface 811. This prevents damage to the casing 7 when the battery charger 800 is repeatedly mounted to the radiographing apparatus 820.

Furthermore, to prevent wear of the casing 7, the contact part of the sliding portion 11 with the bottom surface 811 may be made of a material harder than the bottom surface 811. This prevents damage and wear of the surface of the casing 7 of the radiographing apparatus 820. Thus, damage to the casing when the radiographing apparatus is housed in the battery charger can be prevented in an application of the radiographing apparatus.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2016-091606 filed Apr. 28, 2016, which is hereby incorporated by reference herein in its entirety.

What is claimed is:

1. A radiographing apparatus comprising:
    a radiation detection panel including a rectangular effective image-acquisition area configured to detect radiation; and
    a casing configured to house the radiation detection panel,
    wherein the casing includes an incidence surface on which the radiation is incident, a back surface opposite the incidence surface, and a side surface between the incidence surface and the back surface,
    wherein, on the side surface of the casing, a level-difference portion indicating a position based on the effective image-acquisition area and a protrusion protruding more outward than the level-difference portion are provided, and
    wherein the level-difference portion is disposed at a position corresponding to a center of a side of the effective image-acquisition area.

2. The radiographing apparatus according to claim 1, wherein the protrusion is disposed so as to be held in the level-difference portion in a thickness direction of the casing.

3. The radiographing apparatus according to claim 1, where an area in which the protrusion is provided is larger than an area in which the level-difference portion is provided in a direction in which the side surface of the casing extends.

4. The radiographing apparatus according to claim 1, wherein the protrusion is disposed so as to form an outermost shape of the radiographing apparatus as viewed from a direction of incidence of the radiation.

5. The radiographing apparatus according to claim 1, wherein the level-difference portion comprises a recess.

6. The radiographing apparatus according to claim 1, wherein the casing is formed of a first member constituting an exterior and a second member provided on an inner surface of the first member, and
wherein the protrusion is formed on the side surface of the casing by disposing part of the second member so as to protrude to an outside of the casing.

7. The radiographing apparatus according to claim 1, wherein the level-difference portion is disposed so as not to include a center of the side surface in a thickness direction of the casing.

8. The radiographing apparatus according to claim 1, wherein frictional resistance of the level-difference portion differs from frictional resistance of the protrusion.

9. The radiographing apparatus according to claim 1, wherein the protrusion is disposed so as to coincide with a position of center of gravity of the radiographing apparatus or a center of the radiographing apparatus as viewed from a direction perpendicular to a direction of incidence of the radiation.

10. The radiographing apparatus according to claim 1, wherein the protrusion is disposed at a same position as a radiation detection surface of the radiation detection panel as viewed from a direction perpendicular to a direction of incidence of the radiation.

11. The radiographing apparatus according to claim 1, wherein the side surface of the casing includes an inclined portion inclined in a thickness direction of the casing with respect to the incidence surface or the back surface, and
wherein the level-difference portion is provided on a part of the inclined portion.

12. The radiographing apparatus according to claim 11, wherein, of the level-difference portion, the part provided on the inclined portion is disposed so as not to protrude more outward than the incidence surface as viewed from a direction perpendicular to a direction of incidence of the radiation.

13. The radiographing apparatus according to claim 1, wherein the level-difference portion is disposed on a part of the back surface.

14. The radiographing apparatus according to claim 1, wherein the level-difference portion includes side walls extending inward from the side surface of the casing and a bottom surface disposed between the side walls, and
wherein frictional resistance of the bottom surface of the level-difference portion differs from frictional resistance of the side surface of the casing.

15. The radiographing apparatus according to claim 1, further comprising an operating unit on the side surface, the operating unit being configured to operate the radiographing apparatus,
wherein an outermost periphery of the operating unit is disposed inside an outermost periphery of the casing as viewed from a direction of incidence of the radiation.

16. The radiographing apparatus according to claim 1, further comprising a connection on the side surface, the connection being configured to connect the radiographing apparatus to an external unit,
wherein an outermost periphery of the connection is disposed inside an outermost periphery of the casing as viewed from a direction of incidence of the radiation.

17. A radiographing apparatus comprising:
a radiation detection panel configured to detect radiation; and
a casing configured to house the radiation detection panel,
wherein the casing includes an incidence surface on which the radiation is incident, a back surface opposite the incidence surface, and a side surface between the incidence surface and the back surface,
wherein the casing is formed of a first member constituting an exterior and a second member disposed on an inner surface of the first member, and
wherein, on the side surface of the casing, part of the second member protrudes outward from the casing to form an outer shape of the radiographing apparatus as viewed from a direction of incidence of the radiation, and
wherein the part of the second member is disposed at a position corresponding to a center of a side of the incidence surface.

18. A radiographing system comprising:
a radiographing apparatus; and
a battery charger configured to charge the radiographing apparatus,
wherein the radiographing apparatus comprises:
a radiation detection panel including a rectangular effective image-acquisition area configured to detect radiation; and
a casing configured to house the radiation detection panel,
wherein the casing includes an incidence surface on which the radiation is incident, a back surface opposite the incidence surface, and a side surface between the incidence surface and the back surface,
wherein, on the side surface of the casing, a level-difference portion indicating a position based on the effective image-acquisition area and a protrusion protruding more outward than the level-difference portion are provided, and
wherein the level-difference portion is disposed at a position corresponding to a center of a side of the effective image-acquisition area.

19. The radiographing system according to claim 18, wherein the battery charger includes a contact surface that comes into contact with the protrusion when the radiographing apparatus is housed in the battery charger.

20. The radiographing system according to claim 19, wherein hardness of an outer wall of the casing of the radiographing apparatus is equal to or higher than hardness of the contact surface.

* * * * *